United States Patent
Linares et al.

(10) Patent No.: US 8,840,673 B2
(45) Date of Patent: Sep. 23, 2014

(54) IMPLANTABLE ELBOW JOINT ASSEMBLY WITH SPHERICAL INTER-SUPPORT

(71) Applicants: Miguel A. Linares, Bloomfield Hills, MI (US); Linares Medical Devices, LLC, Auburn Hills, MI (US)

(72) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 11 days.

(21) Appl. No.: 13/624,403

(22) Filed: Sep. 21, 2012

(65) Prior Publication Data

US 2013/0103158 A1   Apr. 25, 2013

Related U.S. Application Data

(60) Provisional application No. 61/537,123, filed on Sep. 21, 2011.

(51) Int. Cl.
*A61F 2/38* (2006.01)
*A61F 2/30* (2006.01)

(52) U.S. Cl.
CPC ....... *A61F 2/3804* (2013.01); *A61F 2002/3021* (2013.01); *A61F 2002/3064* (2013.01); *A61F 2002/30652* (2013.01); *A61F 2002/30642* (2013.01); *A61F 2002/30649* (2013.01); *A61F 2002/30892* (2013.01); *A61F 2002/30878* (2013.01); *A61F 2002/30637* (2013.01); *A61F 2002/30644* (2013.01)
USPC ..................................... 623/20.11

(58) Field of Classification Search
CPC ... A61F 2/3804; A61F 2/3854; A61F 2/4202; A61F 2002/30242; A61F 2002/30649; A61F 2002/3065
USPC .......... 623/20.23, 21.17, 21.18, 19.11–19.14, 623/20.11–20.13, 21.13, 21.16, 17.14, 623/20.22, 22.18
See application file for complete search history.

(56) References Cited

U.S. PATENT DOCUMENTS

| | | | | |
|---|---|---|---|---|
| 807,473 | A | * | 12/1905 | Kolar et al. ................... 446/381 |
| 3,638,243 | A | * | 2/1972 | Campbell et al. .......... 623/20.22 |
| 3,694,821 | A | * | 10/1972 | Moritz ........................ 623/20.22 |
| 3,696,446 | A | * | 10/1972 | Bousquet et al. .......... 623/20.26 |
| 3,795,922 | A | * | 3/1974 | Herbert et al. ............. 623/20.22 |
| 3,837,008 | A | * | 9/1974 | Bahler et al. ............... 623/21.13 |
| 3,868,730 | A | * | 3/1975 | Kaufer et al. .............. 623/20.22 |
| 3,886,601 | A | * | 6/1975 | Findlay ...................... 623/20.22 |
| 3,909,853 | A | * | 10/1975 | Lennox ....................... 623/21.13 |

(Continued)

FOREIGN PATENT DOCUMENTS

GB        2468967 A     9/2010

*Primary Examiner* — Alvin Stewart
(74) *Attorney, Agent, or Firm* — Gifford, Krass, Sprinkle, Anderson & Citkowski, P.C.; Douglas J. McEvoy

(57) ABSTRACT

A multi-component elbow joint assembly incorporated into reconditioned end surfaces established between an upper humerus bone and opposing lower radius and ulna bones. The assembly includes a first component anchored into the upper humerus reconditioned end surface and exhibits a first exposed support surface. A second component is anchored into the lower reconditioned bone end surface of at least one of the radius and ulna bones and exhibits a second exposed support surface. An intermediate component is supported in at least one of eccentric or rotational fashion between the first and second anchored components.

6 Claims, 8 Drawing Sheets

(56) References Cited

U.S. PATENT DOCUMENTS

| | | | |
|---|---|---|---|
| 3,916,451 A | 11/1975 | Buechel et al. | |
| 3,919,725 A | 11/1975 | Swanson et al. | |
| 3,987,500 A * | 10/1976 | Schlein | 623/21.18 |
| 3,992,726 A * | 11/1976 | Freeman et al. | 623/23.4 |
| 4,003,095 A | 1/1977 | Gristina | |
| 4,024,588 A * | 5/1977 | Janssen et al. | 623/18.12 |
| 4,038,704 A * | 8/1977 | Ring | 623/20.11 |
| 4,040,130 A * | 8/1977 | Laure | 623/21.13 |
| 4,079,469 A * | 3/1978 | Wadsworth | 623/20.12 |
| 4,106,128 A * | 8/1978 | Greenwald et al. | 623/21.13 |
| 4,180,871 A * | 1/1980 | Hamas | 623/21.13 |
| 4,206,517 A * | 6/1980 | Pappas et al. | 623/20.13 |
| 4,242,758 A * | 1/1981 | Amis et al. | 623/20.11 |
| 4,257,128 A * | 3/1981 | Scales et al. | 623/20.22 |
| 4,279,041 A * | 7/1981 | Buchholz | 623/19.12 |
| 4,293,963 A | 10/1981 | Gold et al. | |
| 4,378,607 A * | 4/1983 | Wadsworth | 623/20.11 |
| 4,846,840 A * | 7/1989 | Leclercq et al. | 623/22.15 |
| 4,936,848 A * | 6/1990 | Bagby | 623/17.16 |
| 4,950,299 A * | 8/1990 | Noiles | 623/22.18 |
| 5,314,485 A * | 5/1994 | Judet | 623/21.13 |
| 5,507,821 A * | 4/1996 | Sennwald et al. | 623/21.13 |
| 5,702,471 A * | 12/1997 | Grundei et al. | 623/21.16 |
| 5,723,018 A * | 3/1998 | Cyprien et al. | 623/19.13 |
| 5,782,923 A * | 7/1998 | Engelbrecht et al. | 623/20.13 |
| 6,051,751 A * | 4/2000 | Sioshansi et al. | 128/898 |
| 6,117,175 A * | 9/2000 | Bosredon | 623/20.15 |
| 6,290,725 B1 * | 9/2001 | Weiss et al. | 623/20.12 |
| 6,306,171 B1 * | 10/2001 | Conzemius | 623/20.11 |
| 6,379,387 B1 * | 4/2002 | Tornier | 623/20.12 |
| 6,454,808 B1 * | 9/2002 | Masada | 623/21.15 |
| 6,579,321 B1 * | 6/2003 | Gordon et al. | 623/17.16 |
| 6,682,562 B2 * | 1/2004 | Viart et al. | 623/17.14 |
| 6,682,565 B1 * | 1/2004 | Krishnan | 623/21.16 |
| 6,689,169 B2 * | 2/2004 | Harris | 623/21.16 |
| 6,699,290 B1 * | 3/2004 | Wack et al. | 623/20.12 |
| 6,890,357 B2 * | 5/2005 | Tornier | 623/20.12 |
| 7,108,720 B2 * | 9/2006 | Hanes | 623/22.21 |
| 7,160,329 B2 * | 1/2007 | Cooney et al. | 623/20.11 |
| 7,195,644 B2 * | 3/2007 | Diaz et al. | 623/17.13 |
| 7,247,170 B2 * | 7/2007 | Graham et al. | 623/20.13 |
| 7,297,165 B1 | 11/2007 | Kriek | |
| 7,335,231 B2 * | 2/2008 | McLean | 623/22.15 |
| 7,393,362 B2 * | 7/2008 | Cruchet et al. | 623/22.18 |
| 7,419,507 B2 | 9/2008 | Cook et al. | |
| 7,468,076 B2 * | 12/2008 | Zubok et al. | 623/17.11 |
| 7,556,763 B2 * | 7/2009 | Pope et al. | 264/602 |
| 7,566,346 B2 * | 7/2009 | Kirschman | 623/17.14 |
| 7,708,781 B2 * | 5/2010 | Scheker | 623/20.11 |
| 7,780,737 B2 * | 8/2010 | Bonnard et al. | 623/21.11 |
| 7,837,738 B2 * | 11/2010 | Reigstad et al. | 623/21.11 |
| 7,959,678 B2 * | 6/2011 | Filippi et al. | 623/17.14 |
| 8,016,889 B2 * | 9/2011 | Dixon et al. | 623/17.14 |
| 8,070,823 B2 * | 12/2011 | Kellar et al. | 623/23.4 |
| 8,211,175 B2 * | 7/2012 | Eisermann et al. | 623/17.14 |
| 8,292,966 B2 * | 10/2012 | Morton | 623/21.19 |
| 8,333,806 B2 * | 12/2012 | Scheker | 623/21.13 |
| 8,377,066 B2 | 2/2013 | Katrana et al. | |
| 8,449,620 B2 * | 5/2013 | Hakansson et al. | 623/22.16 |
| 8,454,703 B2 * | 6/2013 | Linares | 623/19.13 |
| 8,545,566 B2 * | 10/2013 | Niemiec et al. | 623/17.16 |
| 8,545,571 B2 * | 10/2013 | Collazo et al. | 623/20.27 |
| 8,702,800 B2 * | 4/2014 | Linares et al. | 623/19.13 |
| 8,702,802 B2 * | 4/2014 | Linares et al. | 623/20.21 |
| 2001/0025199 A1 * | 9/2001 | Rauscher | 623/21.13 |
| 2002/0055785 A1 * | 5/2002 | Harris | 623/21.11 |
| 2002/0111690 A1 * | 8/2002 | Hyde | 623/18.12 |
| 2002/0143402 A1 * | 10/2002 | Steinberg | 623/22.16 |
| 2003/0040805 A1 * | 2/2003 | Minamikawa | 623/23.46 |
| 2003/0204261 A1 * | 10/2003 | Eisermann et al. | 623/17.14 |
| 2003/0208277 A1 * | 11/2003 | Weiss et al. | 623/20.12 |
| 2003/0208280 A1 * | 11/2003 | Tohidi | 623/23.39 |
| 2004/0059429 A1 * | 3/2004 | Amin et al. | 623/23.51 |
| 2004/0102853 A1 * | 5/2004 | Boumann et al. | 623/21.16 |
| 2004/0122524 A1 * | 6/2004 | Hunter et al. | 623/22.18 |
| 2004/0225370 A1 * | 11/2004 | Cruchet et al. | 623/22.18 |
| 2005/0149199 A1 * | 7/2005 | Steinberg | 623/22.23 |
| 2005/0158200 A1 * | 7/2005 | Pope et al. | 419/11 |
| 2005/0165490 A1 * | 7/2005 | Tornier | 623/19.13 |
| 2005/0177244 A1 * | 8/2005 | Steinberg | 623/22.17 |
| 2005/0246022 A1 * | 11/2005 | Zubok et al. | 623/17.11 |
| 2006/0004462 A1 * | 1/2006 | Gupta | 623/21.13 |
| 2006/0030946 A1 * | 2/2006 | Ball et al. | 623/21.13 |
| 2006/0095132 A1 * | 5/2006 | Kirschman | 623/17.14 |
| 2006/0100712 A1 * | 5/2006 | Ball | 623/20.13 |
| 2006/0142862 A1 * | 6/2006 | Diaz et al. | 623/17.13 |
| 2006/0173546 A1 | 8/2006 | Berelsman et al. | |
| 2006/0224243 A1 * | 10/2006 | Pare et al. | 623/20.11 |
| 2006/0235414 A1 * | 10/2006 | Lim et al. | 606/73 |
| 2008/0051909 A1 * | 2/2008 | Wolfe et al. | 623/21.12 |
| 2008/0195217 A1 * | 8/2008 | Scheker | 623/20.11 |
| 2008/0215156 A1 * | 9/2008 | Duggal et al. | 623/18.11 |
| 2009/0024221 A1 * | 1/2009 | Ball | 623/20.11 |
| 2009/0281631 A1 * | 11/2009 | Naidu | 623/18.11 |
| 2009/0287309 A1 * | 11/2009 | Walch et al. | 623/18.11 |
| 2009/0292364 A1 * | 11/2009 | Linares | 623/19.13 |
| 2009/0306781 A1 * | 12/2009 | Kyomoto et al. | 623/18.11 |
| 2010/0017966 A1 | 1/2010 | Cho | |
| 2010/0087928 A1 * | 4/2010 | Graham et al. | 623/20.11 |
| 2010/0222887 A1 | 9/2010 | Katrana et al. | |
| 2010/0256770 A1 * | 10/2010 | Hakansson et al. | 623/21.16 |
| 2011/0035012 A1 * | 2/2011 | Linares | 623/18.11 |
| 2011/0035016 A1 * | 2/2011 | Orbay et al. | 623/20.11 |
| 2011/0098822 A1 * | 4/2011 | Walch et al. | 623/19.13 |
| 2011/0106271 A1 * | 5/2011 | Regala et al. | 623/23.4 |
| 2011/0172781 A1 * | 7/2011 | Katrana et al. | 623/20.11 |
| 2011/0238185 A1 * | 9/2011 | Filippi et al. | 623/17.16 |
| 2012/0053697 A1 * | 3/2012 | Palmer et al. | 623/20.12 |
| 2012/0136450 A1 * | 5/2012 | Wendelburg et al. | 623/20.11 |
| 2012/0221113 A1 * | 8/2012 | Katrana et al. | 623/20.12 |
| 2013/0013069 A1 * | 1/2013 | de Villiers et al. | 623/17.15 |
| 2013/0030537 A1 * | 1/2013 | Linares et al. | 623/18.11 |
| 2013/0053969 A1 * | 2/2013 | Linares et al. | 623/19.13 |
| 2013/0053972 A1 * | 2/2013 | Linares et al. | 623/20.28 |
| 2013/0079886 A1 * | 3/2013 | Linares et al. | 623/21.16 |
| 2013/0090738 A1 * | 4/2013 | Linares et al. | 623/21.13 |
| 2013/0090739 A1 * | 4/2013 | Linares et al. | 623/21.18 |
| 2013/0090740 A1 * | 4/2013 | Linares et al. | 623/21.19 |
| 2013/0103158 A1 * | 4/2013 | Linares et al. | 623/20.11 |

* cited by examiner

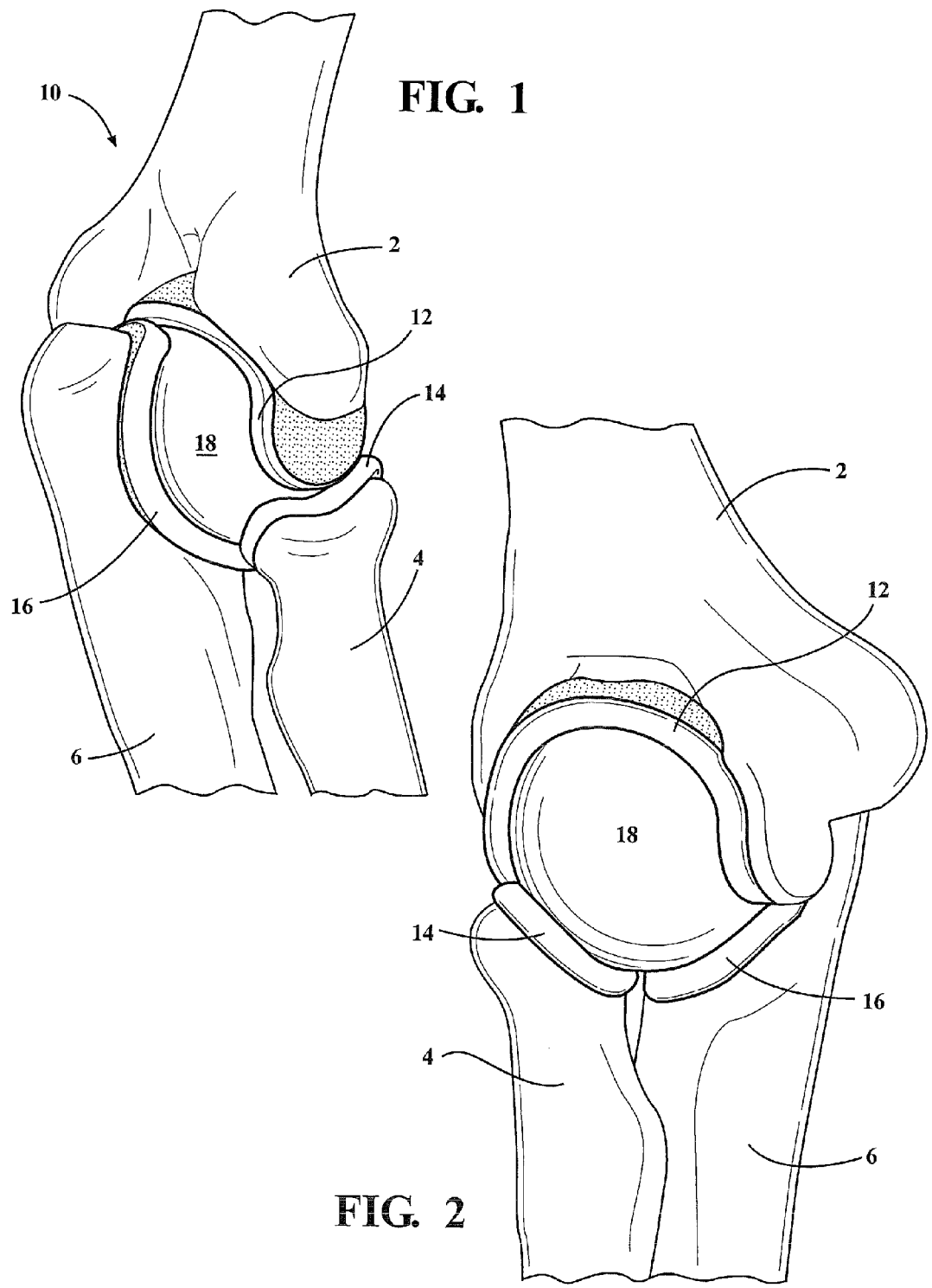

IMPLANTABLE ELBOW JOINT ASSEMBLY WITH SPHERICAL INTER-SUPPORT

The present application claims the priority of U.S. Ser. No. 61/537,123 filed Sep. 21, 2011.

BACKGROUND OF THE INVENTION

1. Field of the Invention

The present invention discloses an artificial joint assembly, such as is particularly configured for employing as a retrofit elbow joint, and which combines multiple artificial components incorporated into first and second reconditioned joint defining surfaces for providing increased wear life in tandem with evenly distributed wear pattern/profile as well as enhanced flexibility and mobility.

2. Background Description of the Prior Art

The prior art is documented with examples of artificial implant assemblies. Among these are included the artificial elbow joint of Ikegami 8,100,980 which teaches a humeral component made of metal and an ulnar component made of resins for replacing an elbow joint. The humeral component is configured by a substantially cylindrical trochlea and a stem extending from the trochlea that is inserted into the humeral. An ulnar component is configured by a joint surface member which receives the trochlea in a rotatable manner and a stem which extends from the joint surface member and is inserted into the ulna. The stem of the humeral component is curved gently downward overall so as to comply with the lordotic shape of the humeral, and the trachea is turnable about the centerline of the stem.

A further example of a minimally thick orthopedic prosthesis which closely matches a minimally reshaped joint defining bone surface by an orbital or lineally oscillating orthopedic resurfacing tool in the minimally invasive orthopedic surgical repair or reconstruction of a variety of joints.

SUMMARY OF THE PRESENT INVENTION

The present invention discloses a multi-component elbow joint assembly incorporated into reconditioned end surfaces established between an upper humerus bone and opposing lower radius and ulna bones. The assembly includes a first component anchored into the upper humerus reconditioned end surface and exhibits a first exposed support surface. A second component is anchored into the lower reconditioned bone end surface of at least one of the radius and ulna bones and exhibits a second exposed support surface. An intermediate component is supported in at least one of eccentric or rotational fashion between the first and second anchored components.

Additional features include the intermediate component having at least one of a spherical shaped or roller shaped component. Each of the anchored components further exhibits a concave surface for supporting the intermediate component.

The anchored components may also include a widened uneven surface for supporting a corresponding uneven profile associated with an intermediate positioned roller. Each of the first, second and intermediate components may be constructed from any of metal, plastic, polymer or composite material.

The arrangement of components can also include a ½ implant assembly associated with a selected side of the joint defining bones. The spherical shaped component may also exhibit a multi layer composition including a softer outer layer and at least one harder interior layer. The first and second inner layers establishes an eccentric rotational interface therebetween.

Additional features include a plurality of surface projecting bearings mounted within an innermost spherical shaped portion of the spherical component for facilitating the eccentric rotational interface. A grid pattern of lubricating grooves may also be defined in a surface of an innermost spherical shaped portion of the spherical component and likewise facilitating the eccentric rotational interface.

BRIEF DESCRIPTION OF THE DRAWINGS

Reference will now be made to the attached drawings, when read in combination with the following detailed description, wherein like reference numerals refer to like parts throughout the several views, and in which:

FIG. 1 is a perspective view of an elbow implant assembly according to a first embodiment of the invention;

FIG. 2 is a rotated perspective view of the assembly in FIG. 1 and better depicting the spherical inter support arranged between upper and lower arm bone end secured implants;

DETAILED DESCRIPTION OF THE PREFERRED EMBODIMENTS

Figure 3:
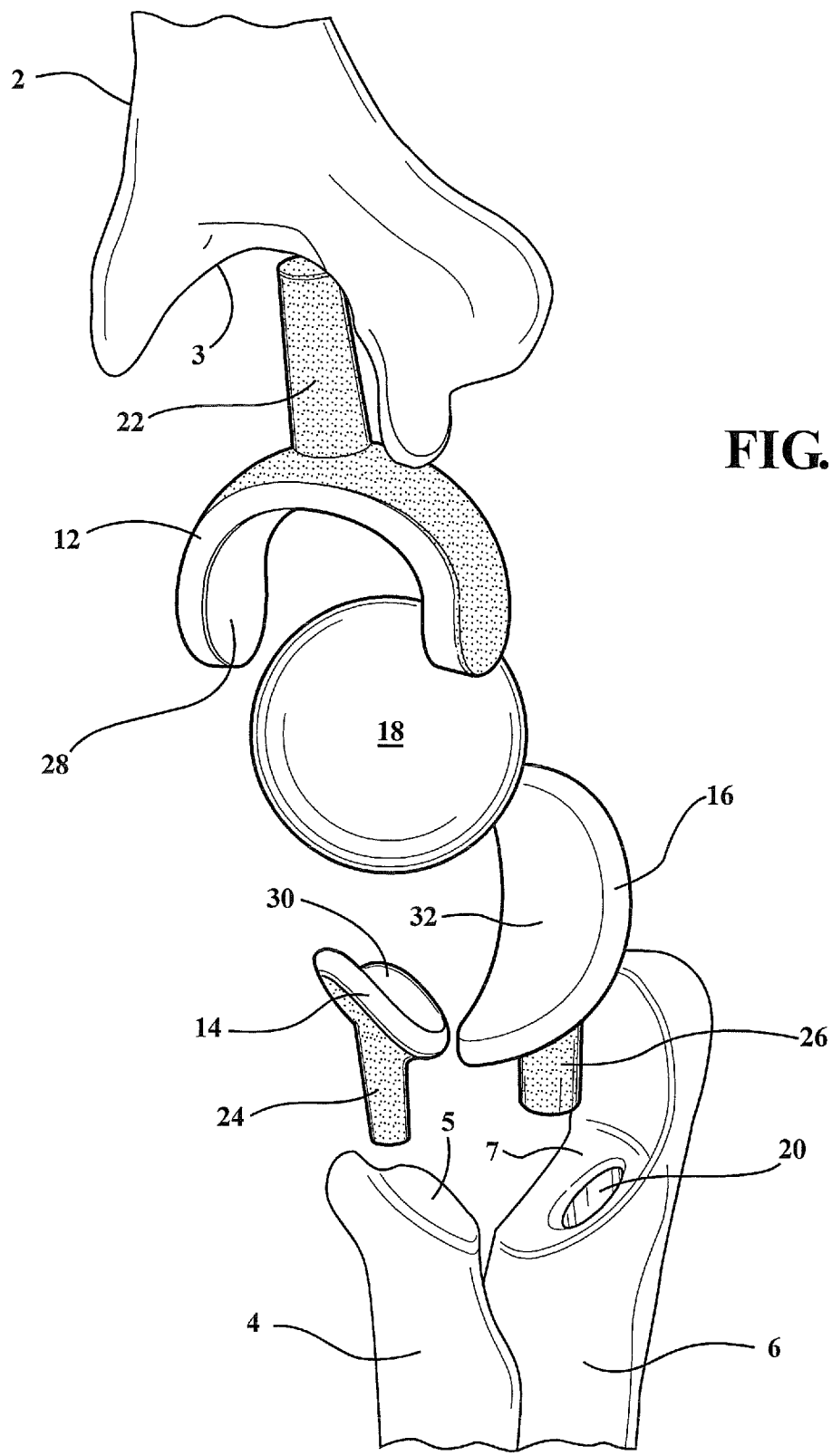
FIG. 3 is an exploded view of the elbow implant assembly of FIG. 1 and better illustrating the reconditioned end-configurations established between the upper humerus and lower radius and ulna arm bones, combined with the implant support inserts and intermediate positioned and eccentrically supported spherical portion.

As will be disclosed with succeeding reference to the several depicted embodiments, the present invention discloses an artificial joint assembly, such as is particularly configured for employing as a retrofit elbow joint, and which combines multiple artificial components incorporated into first and second reconditioned joint defining surfaces for providing increased wear life in tandem with evenly distributed wear pattern/profile as well as enhanced flexibility and mobility.

The joint assemblies described herein are particularly configured for such as in situ reconditioned installation within a patient's elbow (between the lower end of the upper humerus bone and corresponding upper ends of the lower radius and ulna bones), however it is further understood that certain applications could in theory include other joint applications, either human or other mammalian. For purposes of ease and clarify of illustration, the various embodiments depicted further do not include reference to additional necessary components of the elbow joint, such as including associated muscles, tendons and ligaments, the inclusion of which are assumed and which collectively define a functioning and articulating elbow.

Referring now to FIG. 1, a perspective view is generally shown at 10 of an elbow implant assembly according to a first embodiment of the invention and which is incorporated between an upper arm (humerus) bone 2 and a lower arm bones represented by radius 4 and ulna 6. As best shown in the exploded view of FIG. 3, the present invention contemplates such as in situ reconditioning of the bone ends, illustrated by conditioned end profiles 3 configured into the bottom most end surface of the humerus 2, as well as opposing upper end facing and recessed/reconditioned profiles 5 and 7 defined in the upper most opposing ends of the radius 4 and ulna 6.

Such reconditioning occurs following incision or removal of any remaining damaged bone and/or cartilage associated with the damaged joint and during an appropriate surgical procedure utilizing medical drilling, boring and shaping instruments in order to recondition the joint defining bone ends and to create the desired shaping and profile of the joint. As previously indicated, it is advantageous to refashion the joint end profiles in situ during an appropriate surgical procedure, a further objective being to retain or repair, where possible, natural ligament, cartilage and muscle associated with a normal functioning joint.

Figure 4:
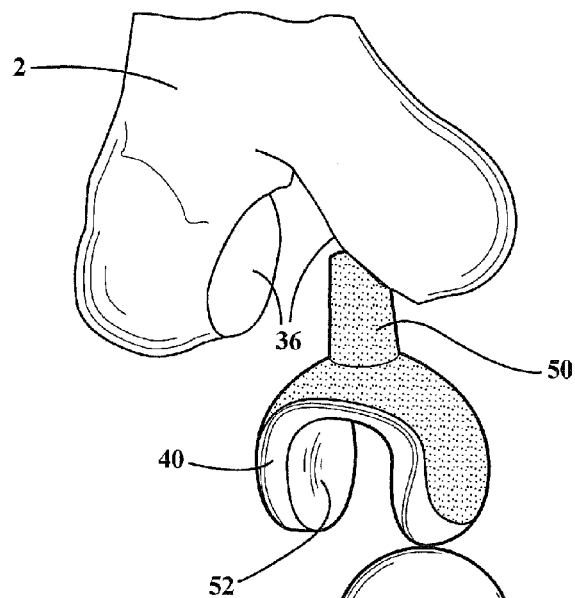
FIG. 4 is a perspective view of a modified and reduced (½) sized elbow implant assembly for installation at the humerus/ulna joint interface.
Figure 5:
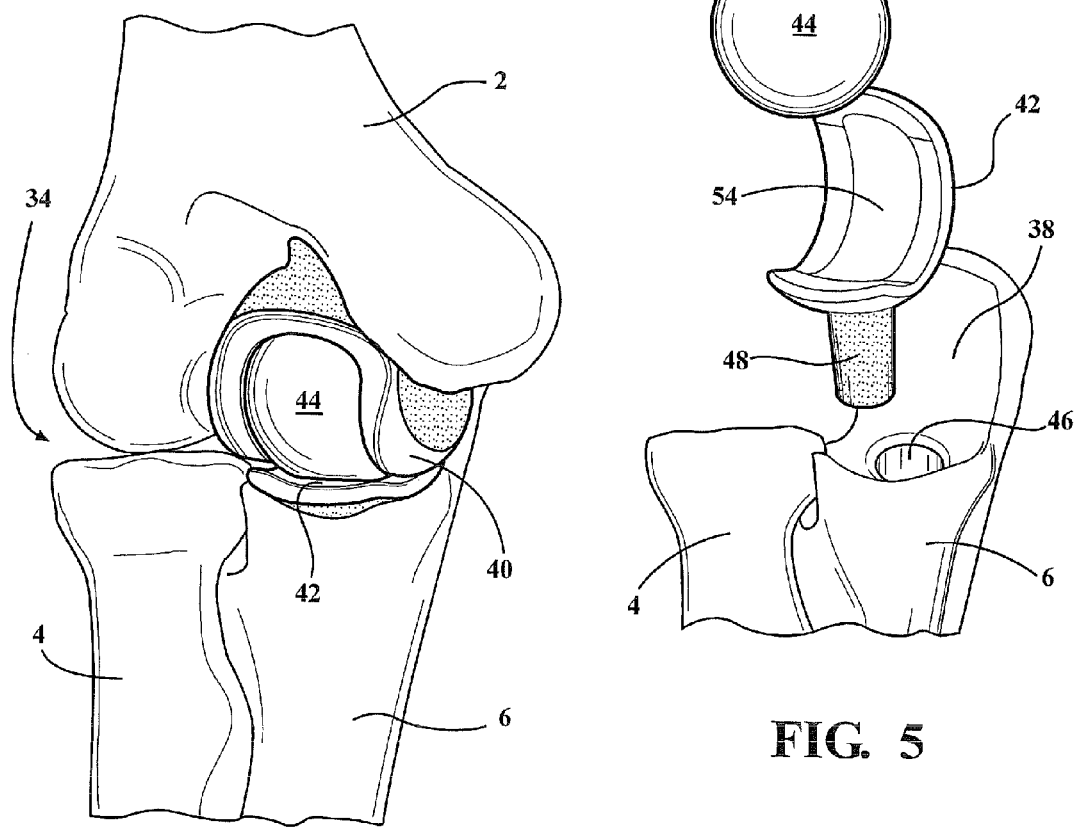
FIG. 5 is an exploded view of the elbow implant assembly in FIG. 4 and again better illustrating the reconditioned end-configurations established between the upper humerus and lower ulna arm bones, combined with the implant support inserts and intermediate positioned and eccentrically supported spherical portion.

Although not shown, such reconditioning can be employed with minimal interference to such necessary additional elements of the elbow joint including associated ligaments, muscles and tendons. Without limitation, it is further understood that the joint assemblies described in each of the illustrated variants can be integrated into either of human or synthetic bones (such as which can also contemplate both human and synthetic bones in a single joint application), with such joint assemblies also capable of surgically implanted in either total or partial fashion (as depicted in FIGS. 4 and 5) concurrent with any necessary degree of refashioning or removal of damaged bone or joint.

Referring again collectively to FIGS. 1-3, the multi-component assembly 10 better illustrates the reconditioned end-configurations 3, 5 and 7 (again FIG. 3) established between the upper humerus 2 and lower radius 4 and ulna 6 bones. A set of bone end installable implant portios are depicted at 12, 14 and 16 with each exhibiting a rear facing profile suitable for anchoring into the respective end face configurations 3, 5 and 7.

Each of the implant portions 12, 14 and 16 are constructed of any arrangement of metal, polymer, plastic, composite or other suitable material, with it further being understood that the individual pairs of components can be arrayed with any pattern of alternating materials, such that the components 12,14 and 16 can be constructed of a first material, with an intermediate and inter-positioned spherical shaped bearing or ball portion 18 positioned therebetween being constructed of a second material. In this fashion, the desired wear properties and profiles are adjusted in part based upon the material selection of the individual components with concurrent objectives being both equalization of overall wear patterns established between the respective pairs of components and determining those situations in which metal on metal or plastic on plastic contact between the components is either desired or, more often, not.

A suitable medical adhesive, cement or other fastener can be employed for securing each of the upper component 12 and lower components 14 and 16 into the respective reconditioned joint defining ends 3, 5 and 7 of the humerus 2, radius 4 and ulna 6. As further best shown in FIG. 3, each of the reconditioned bone ends includes an interior extending aperture, best depicted by selected aperture 20 associated with reconditioned ulna end face 7. In this manner, a rearward extending anchoring stem (see at 22 for upper implant component 12 and further at 24 and 26 for lower implant components 14 and 16) is configured for seating within the associated bone end face interior aperture, thereby assisting in seating the end mounted implants in the manner depicted in FIGS. 1 and 2.

Each of the end face mounted implants 12, 14 and 16 exhibits a concave exterior facing profile (this including a generally modified "U" shaped profile 28 associated with upper implant 12 and corresponding partial 30 and crescent 32 concave shaped profiles. The arrangement of the concave support faces 28, 30 and 32 are such that, upon securing the implants 12, 14 and 16 within the reconditioned end face locations 3, 5 and 7 of the bones 2, 4 and 6, collectively define upper and lower seating locations for supporting the interposed spherical element 18 in a designed range of eccentric articulating fashion.

As further previously noted, the concave spherical supporting faces 28, 30 and 32 can each be constructed of a smooth lubricant entrained or other polished plastic, composite or metal surface, with the exterior configuration of the spherical support 18 again being constructed of an alternating material, such as to reduce and equalize wear profiles, as well as to enhance operational range and effectiveness.

As again previously indicated, additional configurations of muscles, ligaments, tendons are provided and can include both natural and/or synthetic materials which can be implanted or reconstructed in order to provide a dynamic and long-term implantable assembly. Also, the seating or inserting rear faces of the end face mounted implant portions 12, 14 and 16 as best shown in FIG. 3 further include an undercut textured or otherwise roughened consistency, this contributing to promotion of bone marrow in-growth into the implant portions following such as initial adhesive and seating affixation, such bone growth contributing to long term retention of the implant.

FIG. 4 is a perspective view generally at 34 of a modified and reduced (½) sized elbow implant assembly for installation at the humerus/ulna joint interface. In combination with the exploded view of FIG. 5, modified reconditioned end-configurations are depicted at 36 and 38 established between the upper humerus 2 and lower ulna 6 arm bones, combined with implant support inserts (upper 40 and lower 42) and intermediate positioned and eccentrically supported intermediate (and smaller sized in comparison to FIG. 1) spherical portion 44.

As previously described, the implant configuration 34 of FIG. 4 is considered to be a partial implant assembly, such as in which the humerus to radius joint portion may constitute and undamaged and enduring portion of the overall elbow joint and in which the original configuration of ligaments, tendons and muscles (not shown) may remain. As previously also described, the present invention contemplates either retention of such supporting elbow joint structure and/or partial or total replacement of the damaged ligaments, tendons and muscles in the course of an associated joint reconstruction procedure.

As with the prior embodiment, the reconditioned joint end faces (see ulna 6 end face 38) can again include a recessed aperture (define by inner perimeter wall 46) for seating an associated mounting post 48 of the lower implant 42 as well as a corresponding post 50 associated with the upper implant 40 which is otherwise largely similar to the implant 12 depicted in FIG. 3. The upper 40 and lower 42 implants, similar to those described in the initial variant, likewise include concave support surfaces (see pair at 52 and 54) which define eccentric support locations of the interposed spherical ball 44 (see FIG. 4) and such that the partial elbow joint reconstruction exhibits a substantial range of bendable arm motion, combined with limited lateral/eccentric motion. As with the first disclosed variant, the reverse end mounting surfaces of the implants 40 and 42 can again exhibit a textured or undercut consistency which promotes bone in growth over time and to insure against loss of initial contact adhesion resulting from the use of medical cement or the like for anchoring the plasticized, composite or metal implant into the reconditioned bone end faces 36 and 38.

Figure 6:
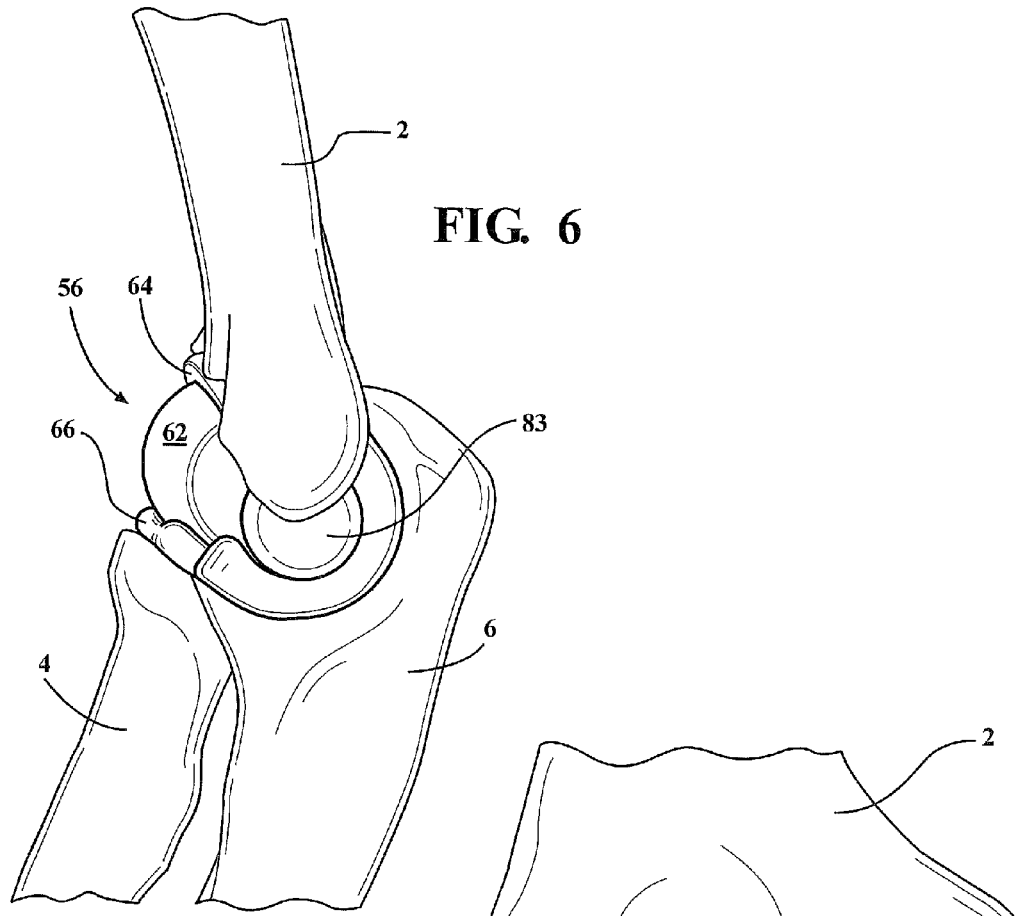
FIG. 6 is a side perspective of an elbow implant assembly according to a yet further preferred variant.
Figure 7:
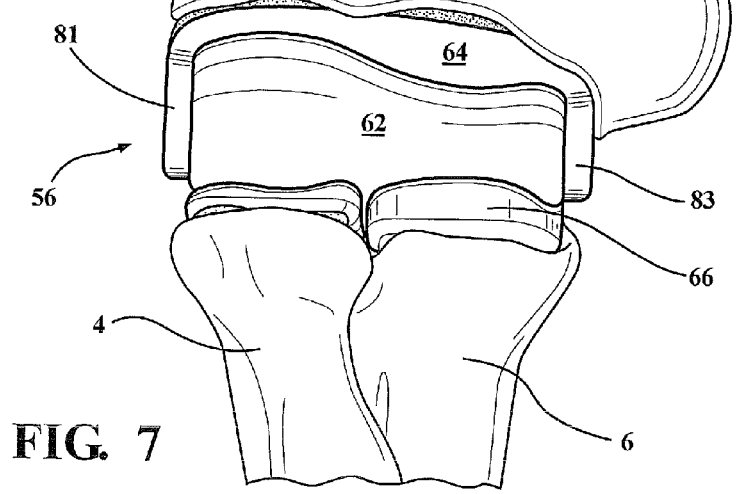
FIG. 7 is a rotated front plan view of the elbow implant assembly of FIG. 6 and better depicting the roller shape associated with the intermediate support element.
Figure 8:
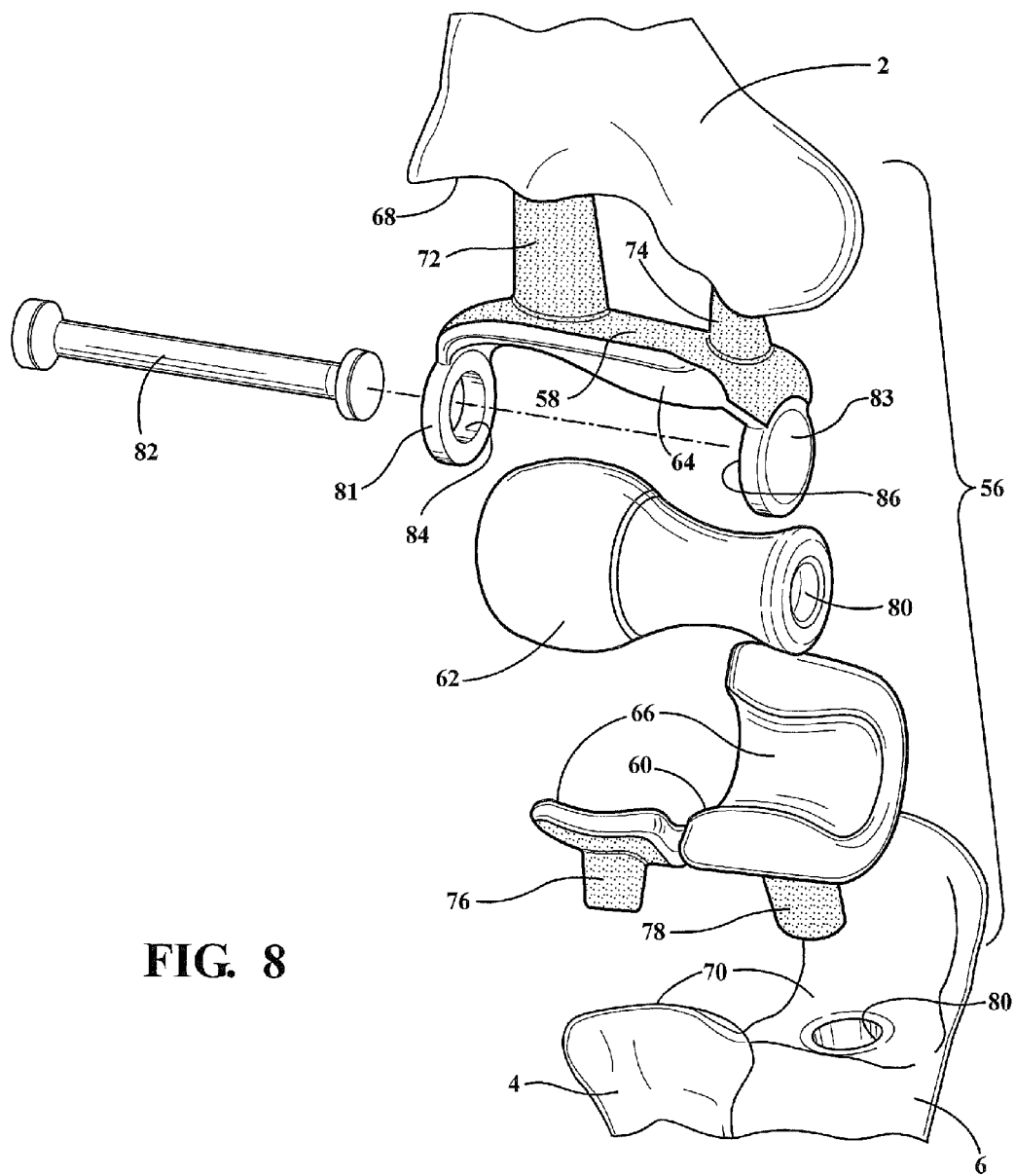
FIG. 8 is an exploded view of the elbow implant assembly of FIGS. 6 and 7 and better illustrating the reconditioned end-configurations established between the upper humerus and lower radius and ulna arm bones, combined with the configuration of the implant support inserts and intermediate positioned and pseudo bowling pin shape associated with the intermediate positioned roller support.

Referring now to FIGS. 6-8 in succession, a series of side perspective, front plan and exploded views are depicted of an elbow implant assembly 56 according to a yet further preferred variant and which combines a further arrangement of end surface attachable implant portions 58 and 60 in combination with an interposed and substantially irregular (e.g. vase like or pseudo bowling pin) shaped roller 62 which seats within concave widened surface profiles 64 and 66. Both the upper humerus 2 and lower radius 4/ulna 6 joint surfaces are again reconditioned, such as shown by profiles 68 and 70 in FIG. 8, and such that the widened implants 58 and 60 are seated in end-anchoring fashion in the manner best depicted in the frontal view of FIG. 7.

As again shown in the exploded view of FIG. 8, the implants 58 and 60 each again include reverse side extending (pairs) of stems (see at 72 and 74 for upper implant 58 and further at 76 and 78 for lower implant 60) for respectively seating within aligning recessed apertures (exemplified at 80 for ulna bone 6) defined in each of the reconditioned elbow joint end faces. As previously described, roughened undercut patterns are exhibited on the reverse adhering faces of the implants 58 and 60 and promote long term bone in-growth to permanently anchor the implants in place.

The width extending and irregular surfaces 64 and 66 associated with the implants 58 and 60 exhibit a combination of both concave and uneven profiles (again FIG. 8) such that the irregular shaped (bowling pin like) roller 62 seats in a mating rotatable fashion therebetween as best depicted in the frontal plan view of FIG. 7. As again best shown in FIG. 8, a central aperture 80 extending longitudinally through an interior of the roller 62 is engaged by a pin shaft 82 upon pre-positioning the roller 62 between a pair of downward extending end lobes 81 and 83 associated with the upper implant 64, the first end lobe 81 including an inner aperture 84 for permitting initial insertion of the shaft 82, with the opposite end located lobe 83 exhibiting an abutting inner end face 86 defining an end stop of the inserting shaft 82 and thereby mounting the roller 62 in a stationary rotatable position.

As with prior embodiments, a suitable arrangement of ligaments, tendons and muscles can be employed for retaining the arrangement of the elbow joint 56, such as in the same fashion as depicted in the earlier variants 10 and 34, and such as which can be (to the extent possible) retained from the original joint construction of the patient and which can be avoided to the extent possible during in situ end face reconditioning and implantation of the joint assembly. As also previously described, the material construction of the various components 58, 60 and 62 can include an arrangement in which either a plastic/composite or metal can be employed in each of the outer implant portions 58 and 60, with the alternating material employed in the construction of the pseudo roller pin shaped element 62.

Figure 9:
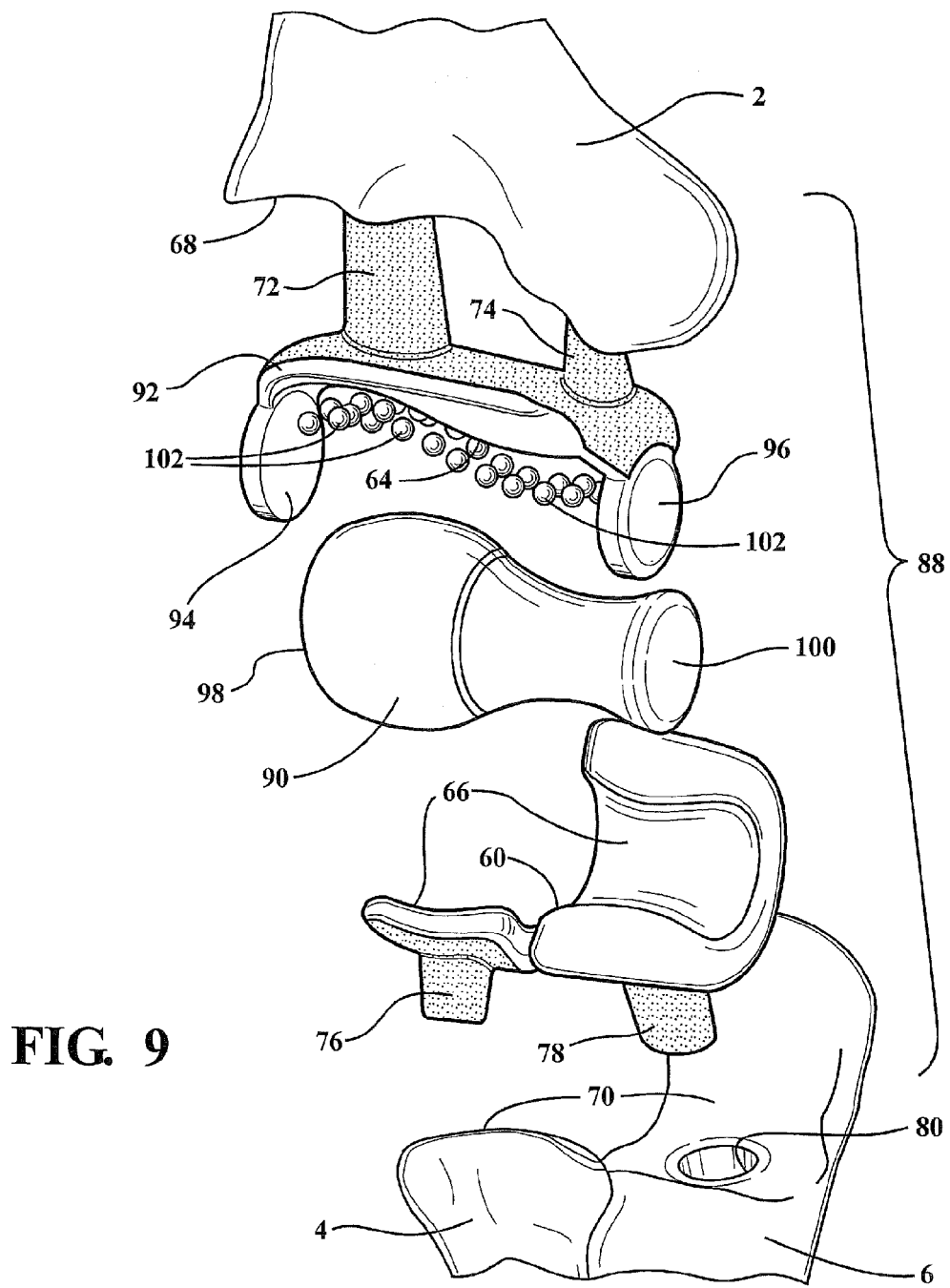
FIG. 9 is a further exploded view similar to as shown in FIG. 8 of a slightly modified variant of roller pin supporting elbow implant assembly and which depicts in further exploded fashion a plurality of ball bearings substantially integrated into the anchored implant associated with the reconditioned end face of the humerus and which provide additional rotational support to the intermediate roller.

Referring now to FIG. 9, a further exploded view similar to as shown in FIG. 8 is presented generally at 88 of a slightly modified variant of roller pin supporting elbow implant assembly and in which the only appreciable differences from FIG. 8 include the provision of a roller pin/uneven shaped roller 90 as a solid component (without internal aperture 80 as in FIG. 8) combined with a reconfigured upper implant 92 with solid end lobes 94 and 96 for snap fitting the opposite end surfaces 98 and 100 therebetween. Although not clearly shown, it is envisioned that the inner facing surfaces of the lobes 94 and 96 can each exhibit one of either a convex or concave shape with alternates with that exhibited by the outer facing end surfaces 98 and 100 of the roller 90, and so as to maintain the roller 90 without the need of the lateral mounting pin shaft 82. The implants 92 and 60 otherwise retain the features of the reverse extending mounting stems 72/74 and 76/78 along with the roughened/undercut bone in-growth promoting reverse surfaces.

Also depicted in FIG. 9 in further exploded fashion are a plurality of, generally micro sized, ball bearings 102. Although not clearly providing an underside view of the concave/irregular pin supporting surface associated with the underside of the implant 92, the bearings 102 are substantially seated in distributed fashion along the humerus end face anchored implant 92 (this defined as being substantially embedded within the concave/irregular support face previously identified at 64 in FIG. 8 of the upper implant 92), and which provides additional rotational support to the intermediate roller 90.

Figure 10:
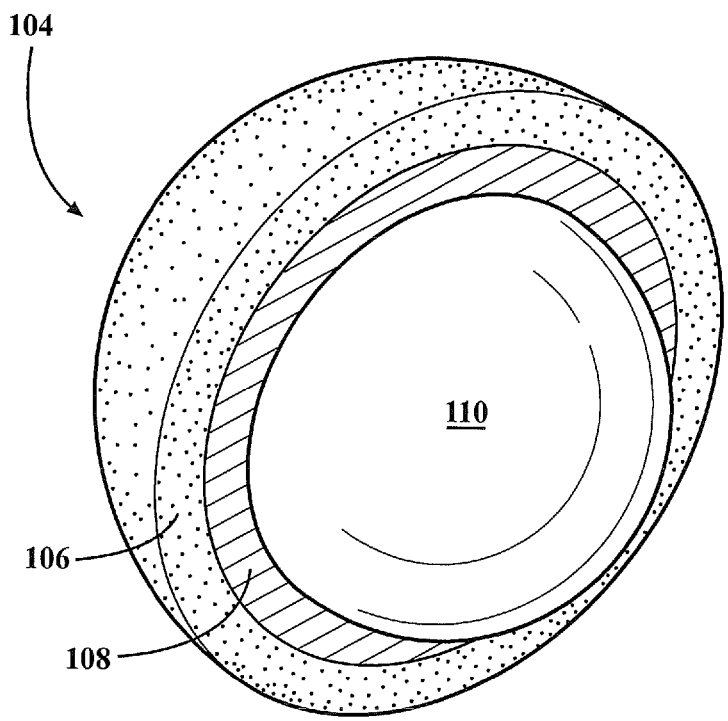
FIG. 10 is a pseudo cutaway view of a spherical shaped intermediate support such as integrated into the variants depicted in FIGS. 1-5, and which illustrates its multi-material construction with softer outermost shell material and intermediate harder material in cutaway, combined with innermost harder core material in spherical perspective and which further evidences an eccentric rotatable interface established between said intermediate and innermost layers.

Referring now to FIG. 10, a cutaway view is generally shown at 104 of a selected spherical inter-movable support, such as again represented by the various spherical balls 18 and 44 respectively disclosed in the variants of FIGS. 1 and 4. The pseudo cutaway view of FIG. 10 illustrates one non-limiting example of a multi-layer material construction and which includes a softer (typically plastic or plastic composite) outermost material layer 106, an intermediate harder 108 material (typically another plastic), and an innermost harder material 110 (which is depicted in un-sectioned spherical perspective shape and can be of a similar hardness as the intermediate layer 108 as well as potentially including either of a relatively harder or softer material based on the specifics and preferences of the application).

In operation, an eccentric rotatable interface is established between the intermediate 108 and innermost (or core) 110 layers, this typically arising from the compressive aspects exerted on the softest outer shell layer 106 by both the upper and lower associated implants resulting in a degree of inter-rotative offset or eccentric give or play established at the interior interface boundary between the intermediate layer 108 and the inner core 110. The outer compressive exerted forces typically result from any inwardly angular directed force exerted on the intermediate spherical element, and such as is defined as a non-tangential force.

Figure 11:
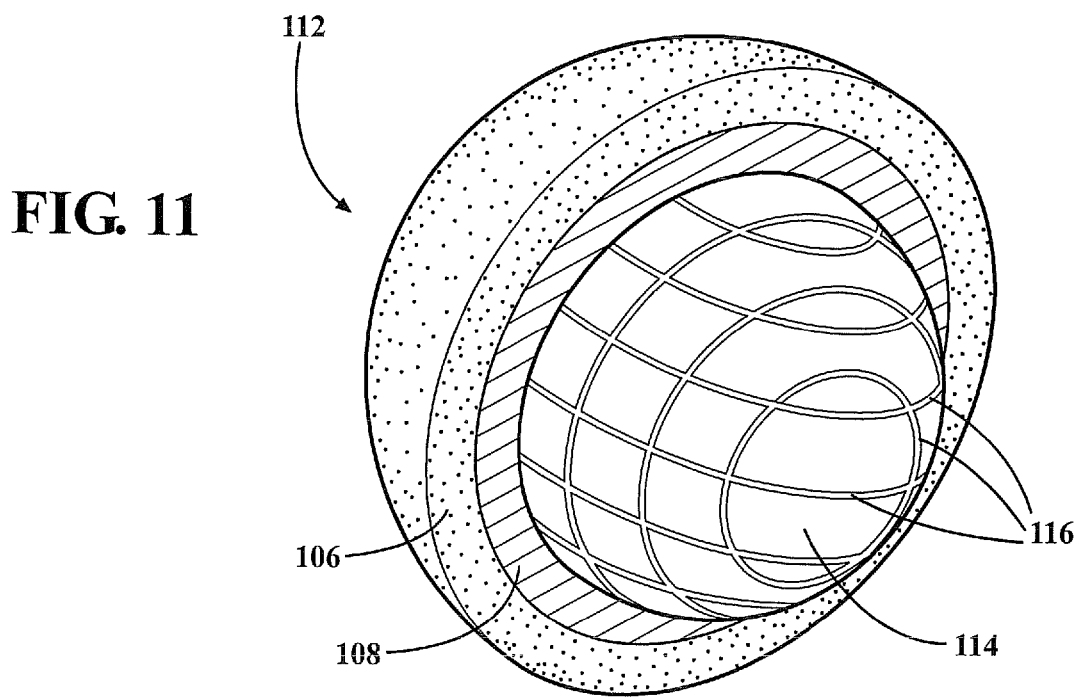
FIG. 11 is a pseudo cutaway view of a spherical shaped intermediate support similar to that in FIG. 10 and further depicting a plurality of lubricant supporting grooves defined in a surface grid pattern associated with the innermost hardened core.

FIG. 11 is a similar pseudo cutaway view, generally at 112, of a spherical shaped intermediate support similar to that in FIG. 10, with identical outer soft shell 106 and intermediate harder shell 108, and in which an innermost core is reconfigured as shown at 114 with a grooved arrangement 116. The grooves 116 can facilitate eccentric motion in the interior boundary defined between layers 108 and 114, in the manner previously described, and/or can also includes entrainment of a volume of lubricant supported within the grooves 116 in a fairly evenly distributed fashion associated with the hardened core 114.

It is also envisioned and understood that the spherical ball, grooves or other supporting structure can include small entrapment channels or pockets for retaining micro particles of debris, either or both plasticized resulting from wear of the implant portions and bone, and such as is further defined as debris osteolysis. The ability to segregate and remove such micro particles (again using the pattern of grooves 116 or other suitable arrangement) assists in extending useful life of the implant along with reducing pain, squeak/noise or other undesirable aspects typical of previous implant designs.

Figure 12:
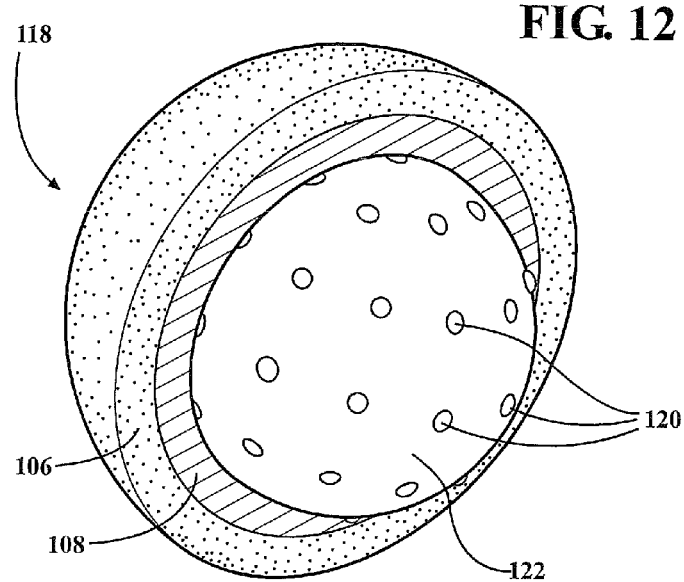
FIG. 12 is a further cutaway view which is again similar to FIG. 10 and further depicting a plurality of substantially surface embedded ball bearings associated with the innermost core.
Figure 13:
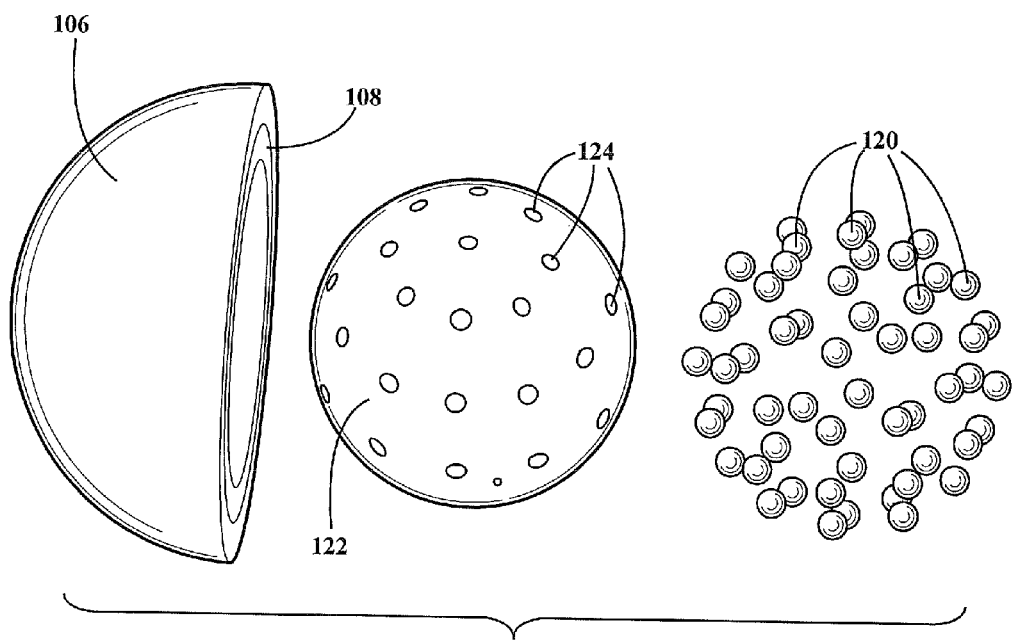
FIG. 13 is an exploded view of the cutaway of FIG. 12 and which better illustrates the arrangement of micro sized ball bearings in combination with the seating locations arranged about the spherical exterior surface of the harder core material.

Referring now to FIG. 12, a further cutaway view is generally shown at 118 which is again similar to FIG. 10 and further depicting a plurality of substantially surface embedded ball bearings 120 associated with a further redesigned version of an inner most core 122. As best depicted in the further exploded view of FIG. 13, the ball bearings 122 are separated from the hardened inner core 122, thereby revealing substantially spherical shaped pockets 124 defined across the exterior profile of the core 122 and which substantially seat the individual bearings 122 in a manner which permits the tips thereof (again FIG. 12) to project in a manner which facilitates additional eccentric support motion with respect to the interior interface boundary established with the intermediate later 108 in a manner consistent with the dynamic environments referenced in relation to FIGS. 10 and 12.

Having described my invention, other and additional preferred embodiments will become apparent to those skilled in the art to which it pertains, and without deviating from the scope of the appended claims.

We claim:

1. A multi-component elbow joint assembly incorporated into reconditioned end surfaces established between an upper humerus bone and opposing lower radius and ulna bones, said assembly comprising:
   a "U" shaped first component anchored into the upper humerus reconditioned end surface and including a first "U" shaped exterior facing profile defining a concave support surface;
   a second component anchored into the lower reconditioned bone end surface of at least one of the radius and ulna bones and exhibiting a second exterior facing profile defining a second concave support surface, said second component further including a pair of components adapted to being secured to each of reconditioned ends of the radius and ulna bones and in opposing and spaced fashion relative opposite perimeter edge locations of said "U" shaped profile; and
   a spherical shaped component supported between said first and second anchored components, said concave shaped support surfaces each contacting said spherical component at separate multi-dimensional locations with an end most location of said second concave support surfaces extending between opposing ends of said first "U" shaped component in order to define a spaced apart relationship between said exterior facing profiles of said first and second concave shaped support surfaces, allowing for multi-axial and eccentric motion of said support surfaces relative to both said spherical component and each other during articulation of the bones about said joint.

2. The joint assembly as described in claim 1, each of said first, second and spherical shaped components further being constructed of at least one of a metal, plastic, polymer or composite material.

3. The joint assembly as described in claim 1, said spherical shaped component further comprising a multi-layer composition including a softer outer-most layer and at least one harder intermediate layer concentrically arranged between said softer outer layer and an exterior surface of said spherical shaped component.

4. The joint assembly as described in claim 3, further comprising said intermediate layer being eccentrically displaceable relative to at least one of said outer layer and said exterior surface of said spherical shaped component and upon a compressive force exerted upon said softer outer layer.

5. The joint assembly as described in claim 4, further comprising a plurality of surface projecting bearings press-fit mounted within substantially spherical shaped pockets formed in said spherical shaped component and such that a portion of each bearing projects from a convex surface of said spherical shaped component and into contact with an inner concave surface associated with said intermediate layer.

6. The joint assembly as described in claim 4, further comprising a grid pattern of lubricant receiving grooves defined in an exterior convex surface of said spherical shaped component in contact with an inner concave surface associated with said intermediate layer.

* * * * *